(12) United States Patent
Ng Choi

(10) Patent No.: US 12,351,558 B2
(45) Date of Patent: Jul. 8, 2025

(54) PROCESS FOR THE SYNTHESIS OF LOFEXIDINE

(71) Applicant: Medichem, S.A., Sant Joan Despí (ES)

(72) Inventor: I-Teng Montserrat Ng Choi, Girona (ES)

(73) Assignee: MEDICHEM, S.A., Sant Joan Despi (ES)

( * ) Notice: Subject to any disclaimer, the term of this patent is extended or adjusted under 35 U.S.C. 154(b) by 469 days.

(21) Appl. No.: 17/913,915

(22) PCT Filed: Apr. 16, 2021

(86) PCT No.: PCT/EP2021/059948
§ 371 (c)(1),
(2) Date: Sep. 23, 2022

(87) PCT Pub. No.: WO2021/209617
PCT Pub. Date: Oct. 21, 2021

(65) Prior Publication Data
US 2023/0123335 A1    Apr. 20, 2023

(30) Foreign Application Priority Data
Apr. 17, 2020  (EP) .................................... 20382310

(51) Int. Cl.
*C07D 233/22*    (2006.01)
(52) U.S. Cl.
CPC .................................. *C07D 233/22* (2013.01)
(58) Field of Classification Search
CPC .................................................. C07D 233/22
See application file for complete search history.

(56) References Cited

U.S. PATENT DOCUMENTS

| | | |
|---|---|---|
| 3,966,757 A | 6/1976 | Baganz |
| 4,443,464 A | 4/1984 | Biedermann et al. |
| 4,518,783 A | 5/1985 | Biedermann et al. |
| 7,652,055 B2 | 1/2010 | Galley et al. |
| 8,101,779 B2 | 1/2012 | Crooks et al. |
| 2011/0015246 A2 | 1/2011 | Digenis et al. |

OTHER PUBLICATIONS

Notification of Transmittal of the International Search Report and the Written Opinion of the International Searching Authority, or the Declaration dated Jun. 18, 2021 for PCT/EP2021/059948.

*Primary Examiner* — Paul V Ward
(74) *Attorney, Agent, or Firm* — Chrisman Gallo Tochtrop LLC

(57) ABSTRACT

The present invention relates to an improved process for the synthesis of lofexidine, or a pharmaceutically acceptable salt thereof, using an aluminium alkoxide as Lewis acid.

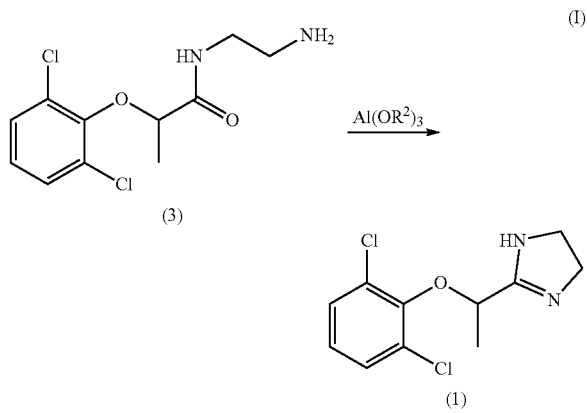

15 Claims, 1 Drawing Sheet

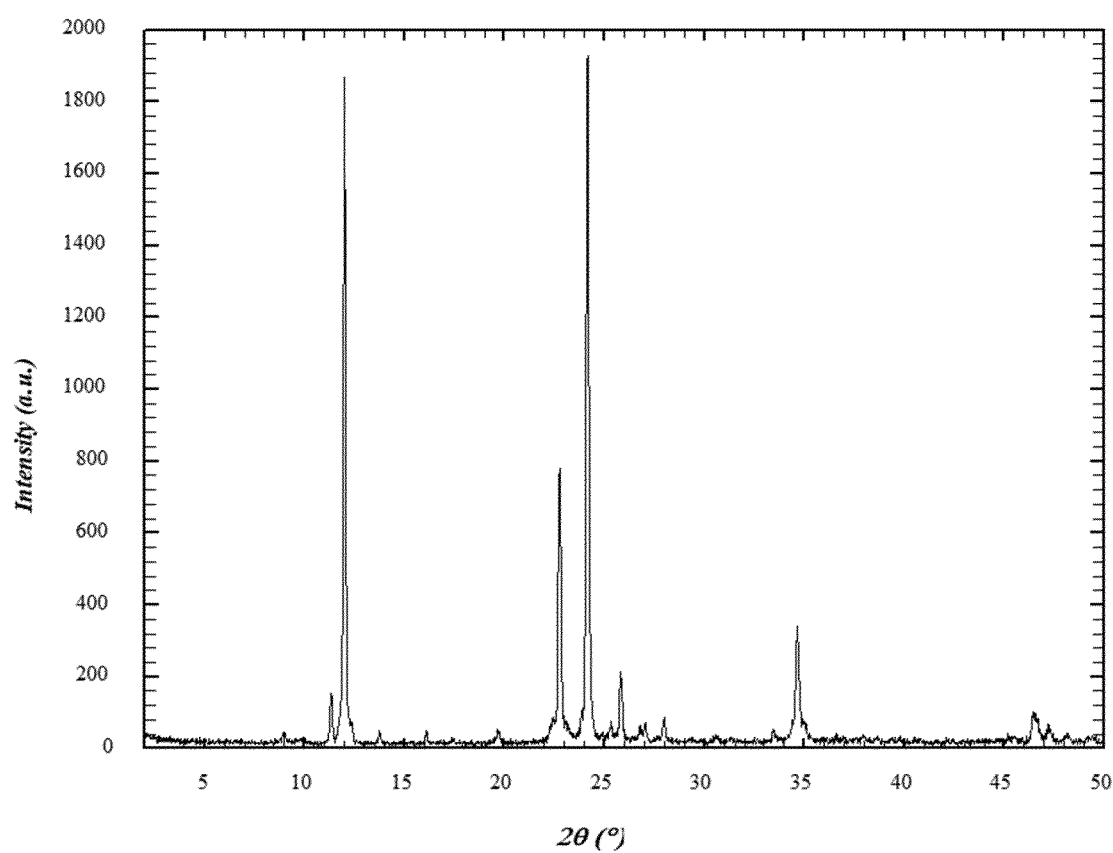

PROCESS FOR THE SYNTHESIS OF LOFEXIDINE

CROSS-REFERENCE TO RELATED APPLICATIONS

This is a National Stage application of PCT international application PCT/EP2021/059948, filed on Apr. 16, 2021, which claims the benefit of European patent application EP20382310.9 filed on Apr. 17, 2020, both of which are incorporated herein by reference in their entirety.

FIELD OF THE INVENTION

The present invention relates to an improved process for the synthesis of lofexidine or a pharmaceutically salt thereof, preferably the hydrochloride salt.

BACKGROUND OF THE INVENTION

Lofexidine, the compound of formula (1), is a central alpha-2 adrenergic agonist that is commercialized as its hydrochloride salt in their racemic form herein referred to as lofexidine hydrochloride, the compound of formula (1) HCl.

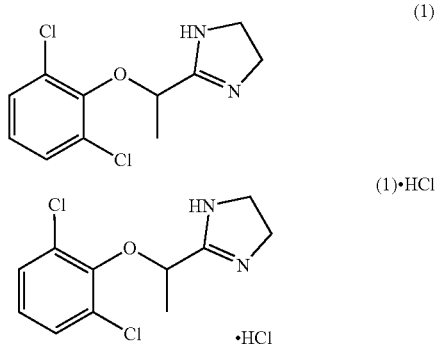

Lofexidine hydrochloride is commercialized by US Worlds in the United States under the brand name of Lucemyra®. Lucemyra® tablets were approved by the FDA on May 2018 as the first non-opioid treatment for management of opioid withdrawal symptoms in adults. Since the 1990s, tablets containing lofexidine hydrochloride are available in the UK market as Britlofex™.

Lofexidine and lofexidine hydrochloride can exist in the dextrorotatory and levorotatory enantiomers, (+)- and (−), respectively.

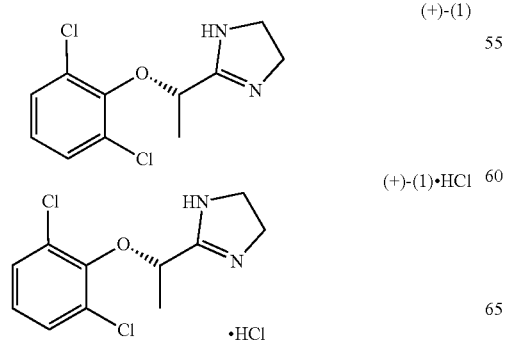

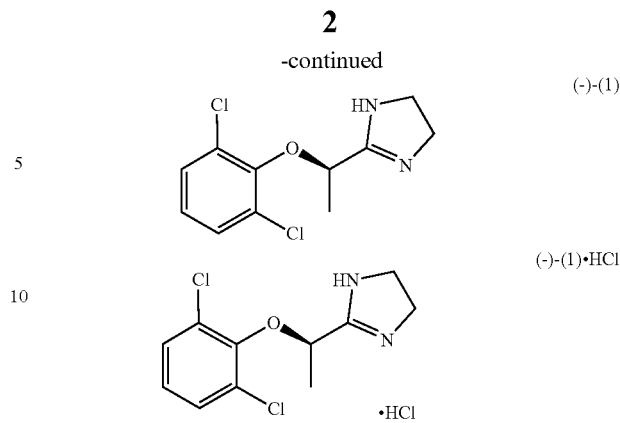

U.S. Pat. No. 3,966,757 discloses the preparation of racemic lofexidine hydrochloride as shown in Scheme 1. In this case, the 2-(2,6-dichlorophenoxy)propionitrile, obtained from the starting compound 2,6-dichlorophenol, was transformed via the Pinner reaction, using ethanol in acidic media, to the corresponding iminoether which was reacted with ethylenediamine to obtain lofexidine hydrochloride. However, this document neither discloses the purity of lofexidine hydrochloride nor the purity of the intermediates thus obtained and does not provide yield data for the last two steps.

Scheme 1

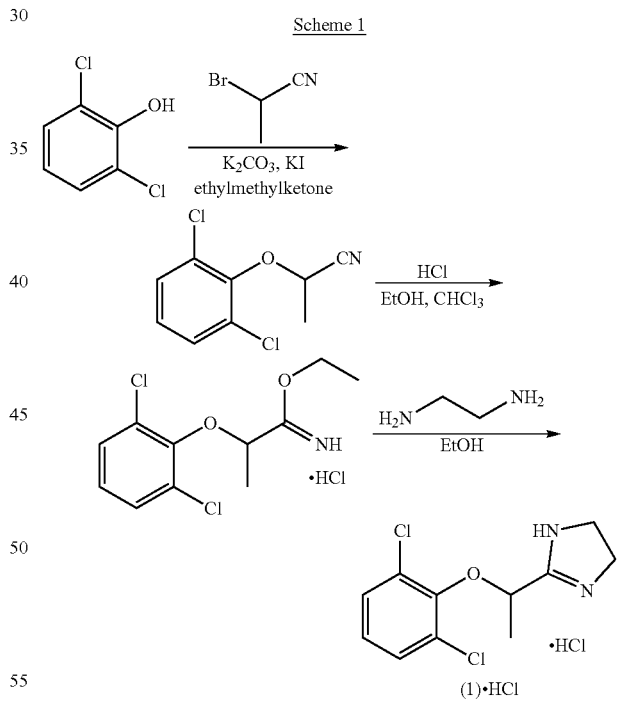

U.S. Pat. Nos. 4,443,464 and 4,518,783 disclose the preparation of enantiomers of lofexidine and lofexidine hydrochloride. U.S. Pat. No. 4,443,464 discloses the preparation of (+)-lofexidine and (+)-lofexidine hydrochloride according to the strategy of synthesis as disclosed in Scheme 2. In the process of example 1 of U.S. Pat. No. 4,443,464, the amidation with ethylenediamine of the ethyl ester intermediate, which is a common reagent also in Example 2, was followed by a Lewis-acid mediated cyclization using a TiCl₄/THF complex in chloroform in the presence of 4-dimethylaminopyridine to obtain, after working up and after purification by column chromatography, (+)-lofexidine which was then converted to (+)-lofexidine hydrochloride salt. This process implies various drawbacks. Not only is chromatographic purification not easily feasible for industrial application, but also the use of TiCl₄ that reacts vigorously with water to generate gaseous HCl. Moreover, an overall yield below 25% was obtained (as calculated from the data given in each process step) and neither the purity of being isolated, with ethylenediamine to obtain (+)-lofexidine which after reacting with HCl yields (+)-lofexidine hydrochloride. However, an overall yield below 25% was obtained (as calculated from the data given in each process step) and neither the purity of (+)-lofexidine and its hydrochloride salt nor the intermediates thus obtained is disclosed. Analogously to this process, the obtention of (−)-lofexidine and (−)-lofexidine hydrochloride salt is disclosed in comparable yield in Example 2 of U.S. Pat. No. 4,518,783.

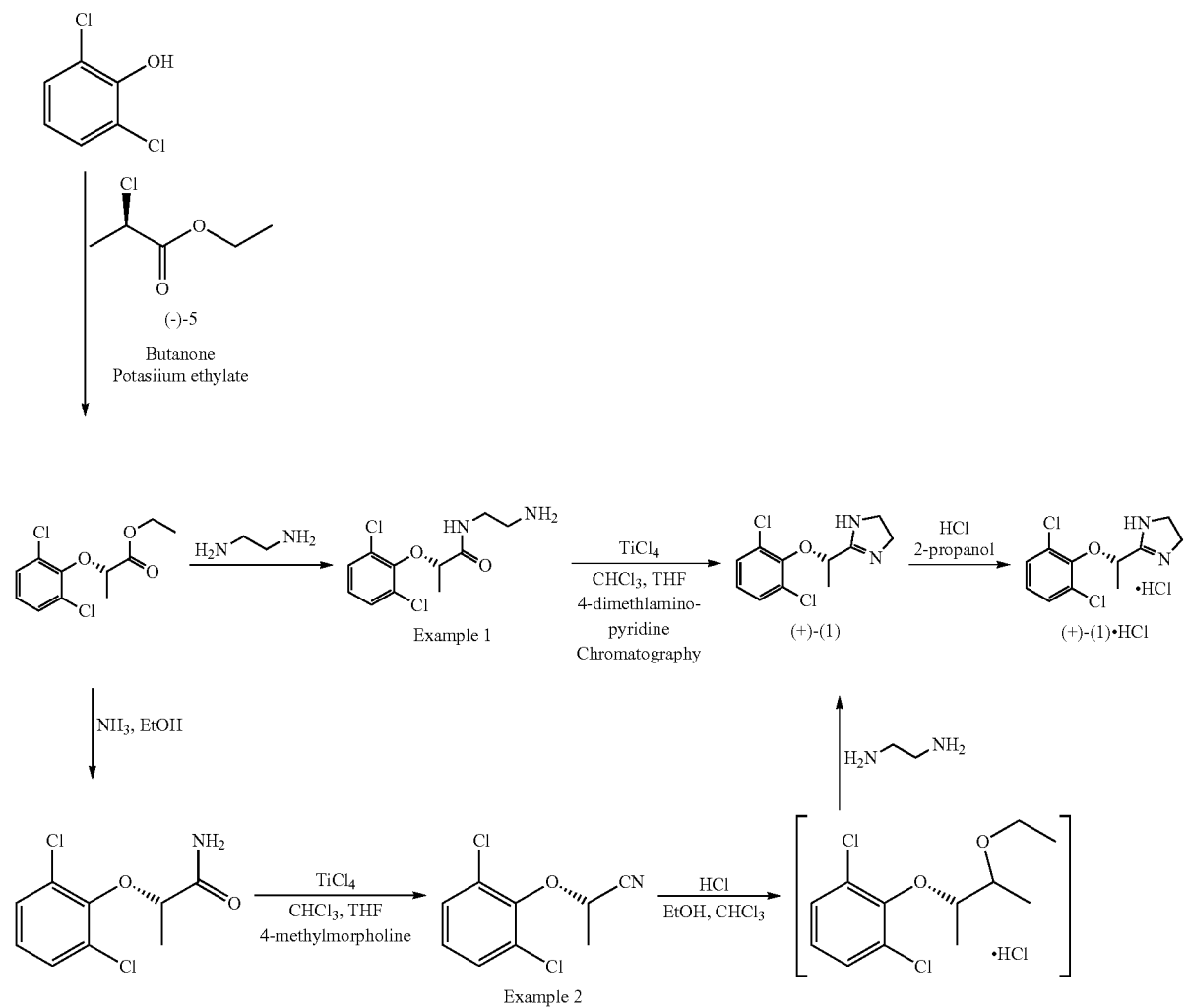

Scheme 2

(+)-lofexidine and its hydrochloride salt nor the intermediates thus obtained is disclosed. Analogously to this process, the obtention of (−)-lofexidine and (−)-lofexidine hydrochloride salt is disclosed in comparable yield in Example 1 of U.S. Pat. No. 4,518,783.

In the process of example 2 of U.S. Pat. No. 4,443,464, the ethyl ester intermediate which is a common reagent also in Example 1, upon reaction with NH₃, was converted to the corresponding amide which was dehydrated with a TiCl₄/THF complex and 4-methylmorpholine in chloroform into (+)-2-(2,6-dichlorophenoxy)propionitrile as shown in Scheme 2. This nitrile compound was transformed via the Pinner reaction, using ethanol in acidic media, to the corresponding iminoether which was reacted in situ, without US20110015246A1 discloses an alternative approach to obtain the (+) and (−) enantiomers of lofexidine. In this case, as shown in Scheme 3, (S)-(+)-lactonitrile was reacted with HCl to form ethyl lactimidate hydrochloride, ethylenediamine was then added to form 2-(1-hydroxyethyl)-2-imidazoline which, after being chlorinated, was reacted with 2,6-dichlorophenol sodium salt to obtain (−)-lofexidine hydrochloride. It is also disclosed that the same process was carried out for the formation of (+)-lofexidine using (R)-(−)-lactonitrile as the starting compound. The main drawback of this process is that it is not exemplified and, consequently, this document is silent on the reaction conditions used (temperature, solvents, etc.), on the characterization of the intermediates and final product thus obtained, and no yield data is provided for any of the process steps.

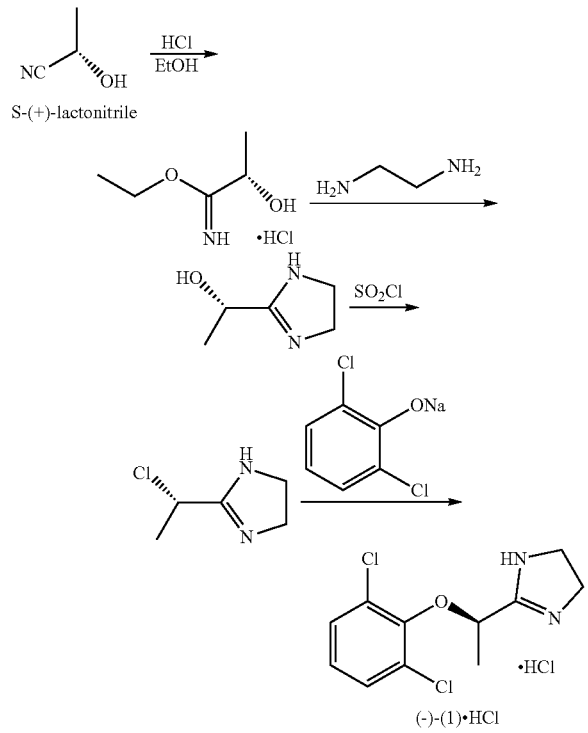

Scheme 3

U.S. Pat. No. 7,652,055B2 discloses the preparation of a generic compound by means of a Markush structure that encompasses lofexidine. In this case, the amidation with ethylenediamine and subsequent Lewis-acid mediated cyclization were carried out in the same synthesis step. Although not specifically disclosed, the process that should be followed for the synthesis of lofexidine would be the one shown in Scheme 4. The main drawbacks of this process are that it is not specifically exemplified and that it is associated with the use of $AlMe_3$ as Lewis-acid, which is a highly flammable and reactive chemical that reacts violently with water to release flammable and explosive gases.

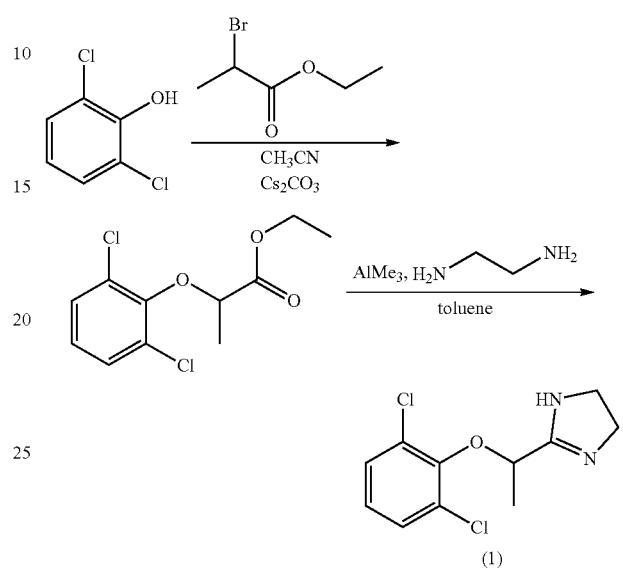

Scheme 4

U.S. Pat. No. 8,101,779B2 discloses another synthetic approach for the synthesis of (−)-lofexidine and its hydrochloride salt as shown in Scheme 5. The process disclosed in this document relies on the transformation in one-pot sequence of an amide compound into an imidazoline compound by the electrophilic alkylation of the amide oxygen by trimethyloxonium tetrafluoroborate ($Me_3O^+BF_4^-$) and subsequent reaction with ethylenediamine. This process is associated with the drawback of using $Me_3OBF_4$, which is a solid that rapidly degrades upon exposure to atmospheric moisture and reacts violently with water.

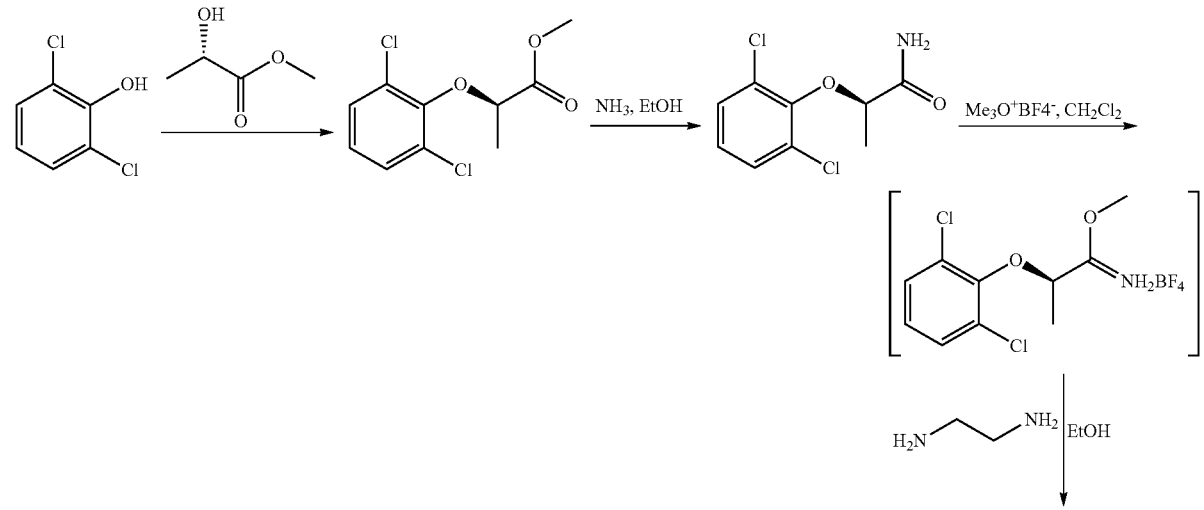

Scheme 5

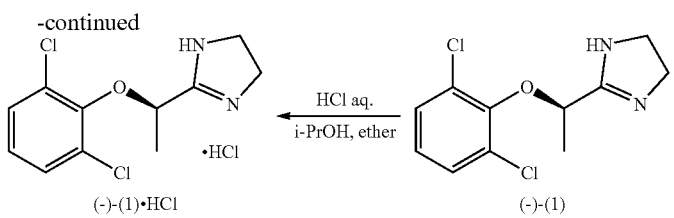

Some of the above prior art documents disclose the preparation of lofexidine, either as a base or as its hydrochloride salt, and either in racemic form or in any of its enantiomers, in low yield, which implies the increase of the cost of the lofexidine process and the pharmaceutical compositions containing this active ingredient, which already resulted in expensive medications. Moreover, some of the above prior art documents disclose the use of explosive and difficult to handle reagents and require purifications by column chromatography.

Therefore, from what is known in the prior art, there is a need in developing a feasible and scalable process for the synthesis of lofexidine or a pharmaceutically acceptable salt thereof, preferably the hydrochloride salt, in high purity and high yield.

SUMMARY OF THE INVENTION

The inventors have found a new process for the preparation of lofexidine and/or a pharmaceutically acceptable salt thereof that overcomes and/or minimizes some of the drawbacks of the processes disclosed in the prior art. The new process allows obtaining these compounds with unexpectedly high overall yields, and at the same time with a high purity. The process is easy to scale-up to an industrial scale and is more cost-effective than the already known processes.

In one aspect of the present invention there is provided a process for preparing lofexidine, the compound of formula (1), or a pharmaceutically acceptable salt thereof, which comprises the step of:

a) converting a compound of formula (3) into lofexidine in a solvent in the presence of an aluminium alkoxide of formula $Al(OR^2)_3$.

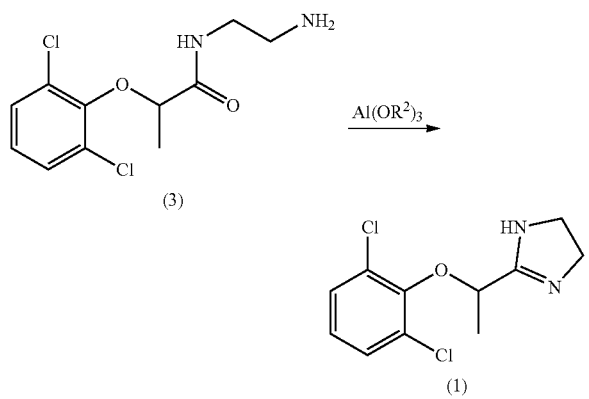

wherein $R^2$ is an alkyl having 1 to 11 carbon atoms, and b) optionally converting the lofexidine into a pharmaceutically acceptable salt thereof.

BRIEF DESCRIPTION OF THE DRAWINGS

FIG. 1 shows the X-Ray Powder Diffractogram of the lofexidine hydrochloride prepared as in Example 10.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims.

A first aspect of the present invention provides a process for preparing lofexidine, the compound of formula (1), or a pharmaceutically acceptable acid addition salt thereof, which comprises the step of:

a) converting a compound of formula (3) into lofexidine in a solvent in the presence of an aluminium alkoxide of formula $Al(OR^2)_3$.

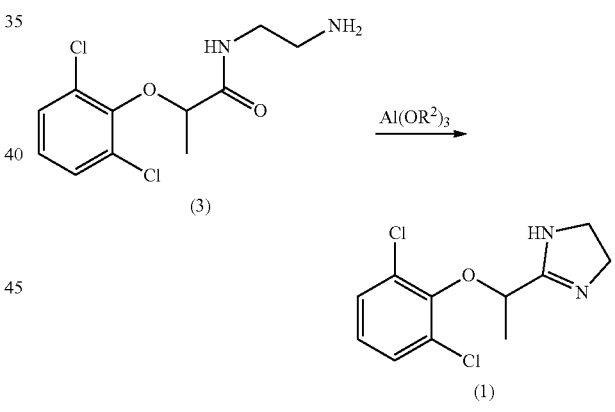

wherein $R^2$ is an alkyl having 1 to 11 carbon atoms, and b) optionally converting the lofexidine into a pharmaceutically acceptable salt thereof.

The authors of the present invention have surprisingly found that the process of the present invention using an aluminium alkoxide of formula $Al(OR^2)_3$ as Lewis acid provides lofexidine or a pharmaceutically salt, preferably lofexidine hydrochloride, in high yields and high purity without the need of using explosive and difficult to handle reagents.

The process allows to obtain lofexidine and a lofexidine salt with high purity and in particular lofexidine hydrochloride, with a purity 99% and with a yield>50%.

In a preferred embodiment of the present invention, the lofexidine obtained in step (a) is converted into a pharmaceutically acceptable salt thereof.

In a preferred embodiment of the present invention, the lofexidine obtained in step (a) is not isolated and is converted in situ into a pharmaceutically acceptable salt thereof.

In a preferred embodiment of the present invention, the pharmaceutically acceptable salt of lofexidine is the hydrochloride salt.

In a preferred embodiment, the lofexidine obtained in step (a) is not isolated and is converted in situ into lofexidine hydrochloride.

Lofexidine and lofexidine hydrochloride may be in any crystalline form. These forms may differ in some physical properties, but they are equivalent for the purposes of the present invention.

The term "pharmaceutically acceptable salt" refers to any salt that possesses the desired pharmacological activity of the parent compound and that is formed from non-toxic pharmaceutically acceptable acids, that include, but are not limited to, organic acids and/or inorganic acids. Such acids include for example hydrochloric, hydrobromic, sulfuric, perchloric, phosphoric, nitric, methanesulfonic, p-toluensulfonic, acetic, trifluoroacetic, propionic, glycolic, lactic, oxalic, malonic, malic, maleic, tartaric, citric, benzoic, cinnamic, mandelic and salicylic acid. Preferably, the pharmaceutically acceptable salt is hydrochloric acid.

Preferably, the step of conversion into a pharmaceutically acceptable salt takes place in the presence of a solvent. More preferably, the reaction takes place in the presence of an organic solvent. Non-limiting examples of organic solvents, which can be used alone or as a mixture of solvents, are alcohols such as methanol, ethanol, isopropanol, n-propanol, n-butanol, isobutanol, sec-butanol or tert-butanol; ketones such as acetone, methyl ethyl ketone or methyl isobutyl ketone; ethers such as tetrahydrofuran, dioxane, diisopropylether, diethylether, 2-methyltetrahydrofuran, cyclopentyl methyl ether or methyl tert-butyl ether; esters such as ethyl acetate, methyl acetate, isopropyl acetate, n-propyl acetate, n-butyl acetate, isobutyl acetate, sec-butyl acetate or tert-butyl acetate; halogenated solvents such as dichloromethane, chloroform, tetrachloromethane, dichloroethane, chlorobenzene or dichlorobenzene; polar aprotic solvents such as N,N-dimethylformamide, acetonitrile, N,N-dimethylacetamide, N-methyl-2-pyrrolidone or dimethylsulfoxide; hydrocarbon aliphatic solvents such as methylcyclohexane, cyclohexane, heptane or hexane; aromatic hydrocarbon solvents such as toluene, benzene, o-xylene, m-xylene or p-xylene; or mixtures of two or more of the solvents listed. Preferably, the reaction takes place in the presence of alcohols, more preferably in the presence of isopropanol.

The lofexidine pharmaceutically acceptable salt may be purified by means of conventional purification techniques, such as crystallization or slurring. Preferably, the lofexidine pharmaceutically acceptable salt may be purified by crystallization.

Aluminium alkoxides of formula $Al(OR^2)_3$ are known compounds that may act as Lewis acids. These compounds may be added either as a solid or they can also be added as a suspension or as a solution. Alternatively, they may be formed in situ by any method known in the art.

The term "alkyl" refers to a straight-chain or branched-chain alkyl group, preferably represents a straight-chain. Alkyl may be unsubstituted or substituted, i.e. optionally substituted by one or more heteroatoms, independently selected from, for example, halogen, oxygen and/or nitrogen. Exemplary substituents include, but are not limited to hydroxy, alkoxy, halogen and amino.

In an embodiment of the present invention, $R^2$ is an alkyl selected from the group consisting of butyl, sec-butyl, tert-butyl and isopropyl.

In a preferred embodiment of the present invention, $R^2$ is isopropyl.

The aluminium alkoxide of formula $Al(OR^2)_3$ when $R^2$ is butyl, sec-butyl, tert-butyl or isopropyl is aluminium tributoxide, aluminium tri-sec-butoxide, aluminium tri-tert-butoxide or aluminium triisopropoxide, respectively.

In a preferred embodiment of the present invention, the aluminium alkoxide of formula $Al(OR^2)_3$ is aluminium triisopropoxide described with the formula $Al(OiPr)_3$.

The amount of aluminium alkoxide of formula $Al(OR^2)_3$ used, preferably aluminium triisopropoxide, is from 1 equivalent to 3 equivalents and more preferably from about 2 equivalents to 3 equivalents, based on the compound of formula (3) used in the preparation of lofexidine, the compound of formula (1).

Suitable solvents in step (a) are solvents as previously defined. Preferably, the solvent used is selected from the group consisting of ethyl acetate, acetonitrile, cyclohexane, N,N-dimethylformamide (DMF), N,N-dimethylacetamide (DMA), dimethyl sulfoxide (DMSO), tetrahydrofuran (THF), toluene, xylene and mixtures thereof. More preferably, the solvent used in step (a) is toluene or xylene and most preferably, the solvent is toluene.

Preferably, the reaction takes place at a temperature from about 50° C. to about 105° C., more preferably from about 70° C. to about 105° C., even more preferably from about 85° C. to about 105° C.

In a preferred embodiment of the present invention, the process for preparing lofexidine, the compound of formula (1), or a pharmaceutically acceptable acid addition salt thereof, further comprises a previous step of reacting a compound of formula (2) with ethylenediamine to provide a compound of formula (3),

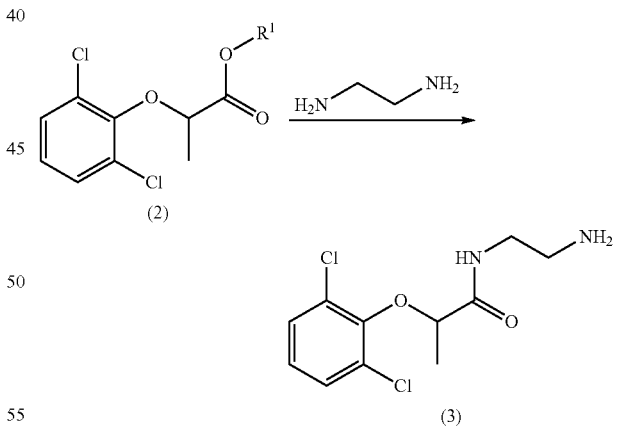

wherein $R^1$ is an alkyl having 1 to 11 carbon atoms.

The compound of formula (3) formed by reacting a compound of formula (2) with ethylenediamine is isolated prior to the conversion step to lofexidine or, alternatively, the compound of formula (3) is converted in situ to lofexidine without isolation.

In a preferred embodiment of the present invention, the compound of formula (3) formed by reacting a compound of formula (2) with ethylenediamine is converted in situ to lofexidine without isolation.

In an embodiment of the present invention, $R^1$ is an alkyl selected from the group consisting of methyl, ethyl and linear or branched propyl, butyl, pentyl, hexyl, heptyl, octyl, nonyl, decyl and undecyl.

In a preferred embodiment of the present invention, $R^1$ is ethyl.

The reaction of compound of formula (2) with ethylenediamine may be carried out either in the presence or absence of a solvent.

Preferably the reaction takes place in the presence of a solvent. Suitable solvents are solvents as previously defined and optionally, in the presence of water. Preferably, the solvent used is selected from the group consisting of ethyl acetate, acetonitrile, cyclohexane, N,N-dimethylformamide (DMF), N,N-dimethylacetamide (DMA), dimethyl sulfoxide (DMSO), tetrahydrofuran (THF), toluene, xylene and mixtures thereof. More preferably, the solvent used is toluene or xylene and most preferably, the solvent used is toluene.

Preferably, the reaction takes place at a temperature from about 50° C. to about 105° C., more preferably from about 70° C. to about 105° C., even more preferably from about 85° C. to about 105° C.

The term "about" or "around" as used herein refers to a range of values±10% of a specified value. For example, the expression "about 10" or "around 10" includes ±10% of 10, i.e. from 9 to 11.

Preferably, the amount of ethylenediamine used is from 1 to less than or equal to 3 equivalents, more preferably about 2 equivalents, based on the compound of formula 2 used in the preparation of the compound of formula (3).

In a preferred embodiment of the present invention, the process for preparing lofexidine, the compound of formula (1), or a pharmaceutically acceptable acid addition salt thereof, comprises the steps of:

i) reacting a compound of formula (2') with ethylenediamine to provide a compound of formula (3),

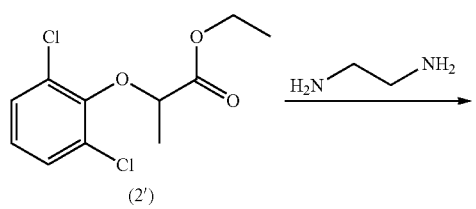

ii) converting a compound of formula (3) into lofexidine in a solvent in the presence of an aluminium alkoxide of formula $Al(OR^2)_3$.

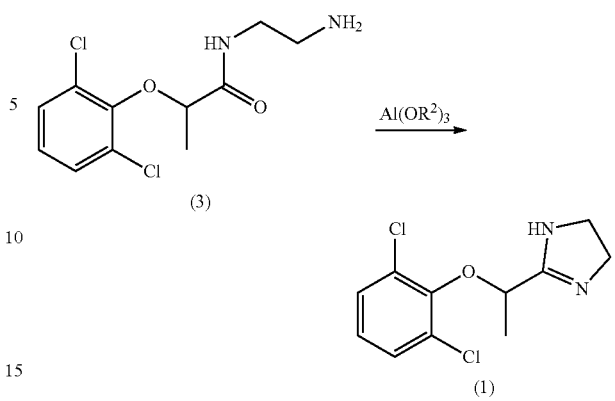

wherein $R^2$ is an alkyl having 1 to 11 carbon atoms, and iii) optionally converting the lofexidine into a pharmaceutically acceptable salt thereof.

In a preferred embodiment of the present invention, the process for preparing lofexidine, the compound of formula (1), or a pharmaceutically acceptable acid addition salt thereof, comprises the steps of:

i) reacting a compound of formula (2') with ethylenediamine to provide a compound of formula (3),

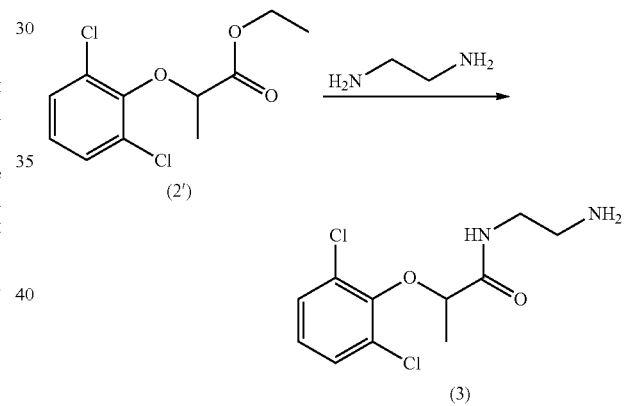

ii) converting a compound of formula (3) into lofexidine in a solvent in the presence of aluminium triisopropoxide $(Al(OiPr)_3)$, and

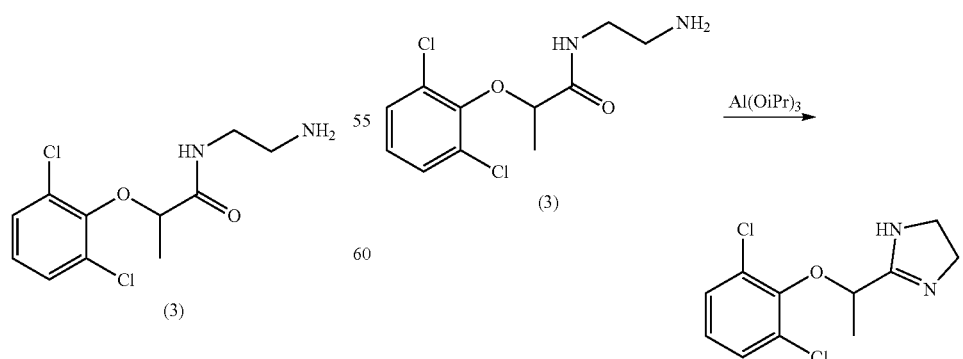

iii) optionally converting the lofexidine into a pharmaceutically acceptable salt thereof.

In a preferred embodiment of the present invention, the compound of formula (3) formed by reacting a compound of formula (2') with ethylenediamine is reacted in situ, without isolation, with an aluminium alkoxide of formula $Al(OR^2)_3$ to obtain lofexidine. The lofexidine thus obtained can be isolated or alternatively can be converted in situ into a pharmaceutically acceptable salt, preferably the hydrochloride salt.

In a most preferred embodiment of the present invention, the compound of formula (3) formed by reacting a compound of formula (2') with ethylenediamine is reacted in situ, without isolation, with aluminium triisopropoxide of formula $Al(OiPr)_3$ to obtain lofexidine. The lofexidine thus obtained can be isolated or alternatively can be converted in situ into a pharmaceutically acceptable salt, preferably the hydrochloride salt.

The starting material of compound (2) may be commercially available or can be prepared by any method known in the state of the art.

In another embodiment of the present invention, the process for preparing lofexidine as defined above further comprises a previous step of reacting of 2,6-dichlorophenol, the compound of formula (4), or a salt thereof, in particular an alkaline salt thereof, with a compound of formula (5) in the presence of a solvent to prepare the compound of formula (2).

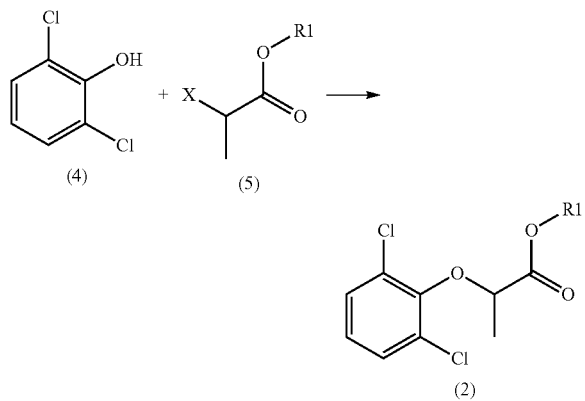

wherein $R_1$ is an alkyl having 1 to 11 carbon atoms and X is a leaving group.

The term "alkaline salt" refers to any salt in which the cation is an alkali metal ion. In an embodiment of the present invention the alkaline salt is selected from the group consisting of lithium salt, sodium salt, potassium salt and cesium salt.

In a preferred embodiment of the present invention, the compound of formula (4) is used in the form of an alkaline salt which is the potassium salt.

Alkaline salts of 2,6-dichlorophenol used can be commercially available or, alternatively, can be formed in situ under the reaction conditions.

The preparation of alkaline salts of 2,6-dichlorophenol in situ can be carried out by methods known in the art. Generally, such salts are prepared, for example, by reacting 2,6-dichlorophenol with an amount of an appropriate inorganic base in water, or in an organic solvent, or a mixture thereof. Non-limiting examples of bases are potassium carbonate, sodium hydroxide, potassium hydroxide, cesium carbonate and potassium hydrogen carbonate. Preferably, the inorganic base used is potassium carbonate in an amount from 0.5 to less than or equal to 3 equivalents based on the amount of 2,6-dichlorophenol, compound of formula (4), used. More preferably, the amount of potassium carbonate used is 0.5 equivalents, based on the amount of 2,6-dichlorophenol, compound of formula (4), used.

Preferably, the solvent used is an organic solvent such as ethyl acetate, acetonitrile, toluene, ethyl methyl ketone, cyclohexane, N,N-dimethylformamide (DMF), N,N-dimethylacetamide (DMA), dimethyl sulfoxide (DMSO), and mixtures thereof. More preferably, the solvent used is dimethyl sulfoxide (DMSO).

In an embodiment of the present invention, $R^1$ is an alkyl selected from the group consisting of methyl, ethyl and linear or branched propyl, butyl, pentyl, hexyl, heptyl, octyl, nonyl, decyl and undecyl.

In a preferred embodiment of the present invention, $R^1$ is ethyl.

The term "leaving group" refers to an electron-withdrawing atom or group of atoms activating the carbon to which they are attached against a nucleophilic reagent, such that said nucleophile, or part of said nucleophile, reacts with the molecule and the leaving group is detached therefrom. Preferably, the leaving group is Cl, Br, I, methanesulfonate, trifluoromethanesulfonate, p-toluenesulfonate and benzenesulfonate More preferably, the leaving group is Cl.

Preferably, the reaction takes place at a temperature from about 10° C. to about 95° C., more preferably from about 50° C. to about 80° C., even more preferably from about 60° C. to about 65° C.

In a preferred embodiment of the present invention, the process for preparing lofexidine as defined above further comprises a previous step of reacting 2,6-dichlorophenol, the compound of formula (4) or a salt thereof, in particular an alkaline salt thereof, with a compound of formula (5') in the presence of a solvent to prepare the compound of formula (2').

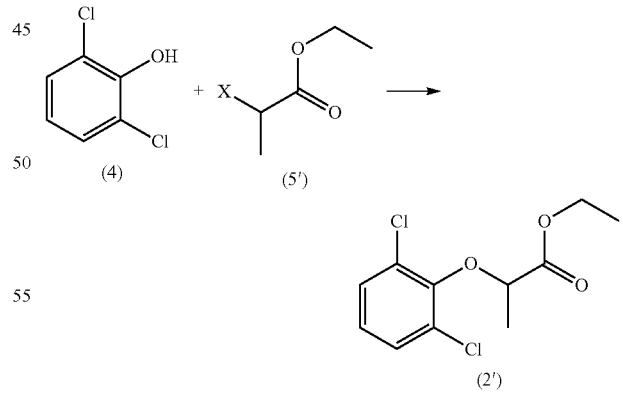

In a preferred embodiment of the present invention, the process for preparing lofexidine as defined above further comprises a previous step of reacting 2,6-dichlorophenol, the compound of formula (4) or a salt thereof, in particular an alkaline salt thereof, with a compound of formula (5″) in the presence of a solvent to prepare the compound of formula (2').

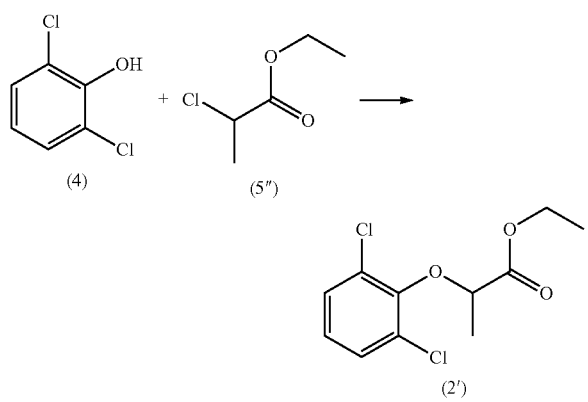

EXAMPLES

Hereinafter, the present invention is described in more detail and specifically with reference to the Examples, which however are not intended to limit the present invention.

X-Ray Powder Diffraction (XRPD):

The XRPD pattern was recorded on a Siemens D5000 diffractometer equipped with two symmetrically mounted vertical goniometers (Bragg-Brentano geometry) with horizontal sample stages, an X-ray tube, a high voltage generator (working at 45 kV and 35 mA) and standard scintillation detectors. Ni-filtered Cu-anode source was used, and diffracted radiation was further monochromatized with a graphite crystal to avoid fluorescence effects [($\lambda(K_\alpha)$ =1.54056 Å]. The diffraction pattern was recorded including values of 2θ that range from 2 to 50° with a sampling rate of 0.02° per second and a step time of 1 second per step. The powdered sample was pressed between two glass plates, forming a film. DIFFRAC Plus measurement software with EVA evaluation software (Bruker) was used to record the data and for a primary analysis of the diffraction pattern. The equipment was periodically calibrated using quartz and silicon.

Example 1: Preparation of Ethyl 2-(2,6-Dichlorophenoxy)Propanoate Compound 2'

20.0 g of 2,6-dichlorophenol were dissolved in 300 mL of dimethyl sulfoxide at 20-25° C., under nitrogen atmosphere. 8.4 g of potassium carbonate were added at 20-25° C. while stirring. 16.7 g of ethyl 2-chloropropionate were then added to the resulting suspension and the resulting mixture was stirred for 4 hours at 60-65° C. After cooling it down to 20-25° C., 300 mL of toluene followed by 300 mL of deionised water were added. The resulting mixture was allowed to settle and a biphasic solution was obtained. The aqueous layer was removed, and after two consecutive washes using an aqueous solution of potassium carbonate 10% (w/w) and a final wash with deionised water, the resulting organic layer was collected and concentrated to dryness under reduced pressure to obtain ethyl 2-(2,6-dichlorophenoxy)propanoate as a liquid. Yield: 92.3%. Purity (HPLC): 99.49%.

Example 2: Preparation of Ethyl 2-(2,6-Dichlorophenoxy)Propanoate Compound 2'

5.0 g of 2,6-dichlorophenol were dissolved in 75 mL of acetonitrile at 20-25° C., under nitrogen atmosphere. 6.32 g of potassium carbonate were added at 20-25° C. while stirring. 5.58 g of ethyl 2-chloropropionate were then added to the resulting suspension and the resulting mixture was stirred for 3 hours at reflux temperature. After cooling it down to 20-25° C., the organic solvent was concentrated to dryness under reduced pressure and then, 25 mL of ethyl acetate followed by 25 mL of deionised water were added to the residue obtained. The resulting mixture was allowed to settle and a biphasic solution was obtained. The organic phase was separated and the aqueous layer was washed with 25 mL of ethyl acetate. After discarding the aqueous phase, the organic layers were collected and washed with brine, and the organic solvent was concentrated under reduced pressure to dryness to obtain ethyl 2-(2,6-dichlorophenoxy)propanoate as a liquid. Yield: 95.3%. Purity (HPLC): 97.76%.

Example 3: Preparation of N-(2-Aminoethyl)-2-(2,6-Dichlorophenoxy)Propanamide Compound 3)

5.0 g of ethyl 2-(2,6-dichlorophenoxy)propanoate obtained in example 1 were suspended in 12.69 mL of ethylenediamine at 20-25° C., under nitrogen atmosphere. The resulting mixture was heated up to reflux temperature and stirred for 2 hours at this temperature. After cooling it down to 20-25° C., 25 mL of ethyl acetate and 25 mL of deionised water were added. The resulting mixture was allowed to settle and a biphasic solution was obtained. The organic phase was separated and the aqueous layer was washed with 25 mL of ethyl acetate. After discarding the aqueous phase, the organic layers were collected and 25 mL of HCl 2N were added. The aqueous layer was extracted and the resulting organic layer was concentrated to dryness under reduced pressure to obtain N-(2-aminoethyl)-2-(2,6-dichlorophenoxy)propanamide as a liquid. Yield: 79.9%. Purity (HPLC): 95.62%.

Example 4: Preparation of 2-(1-(2,6-Dichlorophenoxy)Ethyl)-4,5-Dihydro-1H-Imidazole (Lofexidine Base) Compound 1)

A solution of 20 g of ethyl 2-(2,6-dichlorophenoxy)propanoate in 80 mL of toluene was added to a solution of 31.1 g of aluminium isopropoxide and 9.1 g of ethylenediamine in 220 mL of toluene at 20-25° C. while stirring under nitrogen atmosphere. The resulting mixture was heated up to 105° C. and stirred at this temperature until the reaction was completed. The mixture was cooled down to 10-15° C. Then, 10 g of celite and 32 mL of isopropanol were added, followed by the dropwise addition of 120 mL of deionised water at 10-15° C. The resulting mixture was stirred for 1 hour at 20-25° C. and the resulting solid was filtered. The filtered solution was allowed to settle and a biphasic mixture was obtained. Then, the aqueous layer was removed and the resulting organic layer was concentrated under reduced pressure to dryness to obtain Lofexidine base as a wet solid.

Example 5: Preparation of 2-(1-(2,6-Dichlorophenoxy)Ethyl)-4,5-Dihydro-1H-Imidazole Monohydrochloride (Lofexidine Hydrochloride) Compound 1·HCl A solution of 20 g of ethyl 2-(2,6-dichlorophenoxy)propanoate in 80 mL of toluene was added to a solution of 31.1 g of aluminium isopropoxide and 9.1 g of ethylenediamine in 220 mL of toluene at 20-25° C. while stirring under nitrogen atmosphere. The resulting mixture was heated up to 105° C. and stirred at this temperature until the reaction was completed. The mixture was cooled down to 10-15° C. Then, 10 g of celite and 32 mL of isopropanol were added, followed by the dropwise addition of 100 mL of deionised water at 10-15° C. The resulting mixture was stirred for 1 hour at 20-25° C. and the resulting solid was filtered. The filtered solution was allowed to settle and a biphasic mixture was obtained. Then, the aqueous layer was removed and the resulting organic layer was washed with 60 mL of deionised water. After heating the resulting organic solution up to 45-50° C., a solution of 3.0 g of hydrogen chloride gas in 19.6 mL of isopropanol was added dropwise and the resulting mixture was stirred for a minimum of 30 minutes at this temperature. The resulting suspension was stirred for 1 hour at 20-25° C. followed by 1 hour at 10-15° C. The precipitated solid was filtered and washed with toluene to obtain a wet solid. Yield: 66.9%. Purity (HPLC): 99.28%.

Example 6: Preparation of 2-(1-(2,6-Dichlorophenoxy)Ethyl)-4,5-Dihydro-1H-Imidazole Monohydrochloride (Lofexidine Hydrochloride) Compound 1 HCl A solution of 15 g of ethyl 2-(2,6-dichlorophenoxy) propanoate in 60 mL of xylene was added to a solution of 23.3 g of aluminium isopropoxide and 6.9 g of ethylenediamine in 165 mL of xylene at 20-25° C. while stirring under nitrogen atmosphere. The resulting mixture was heated up to 105° C. and stirred at this temperature until the reaction was completed. The mixture was cooled down to 0-5° C. Then, 7.5 g of celite and 24 mL of methanol were added, followed by the dropwise addition of 90 mL of deionised water at 0-5° C. The resulting mixture was stirred for 1 hour at 20-25° C. and the resulting solid was filtered. The filtered solution was allowed to settle and a biphasic mixture was obtained. Then, the aqueous layer was removed. After heating the resulting organic solution up to 35° C., a solution of 2.5 g of hydrogen chloride gas in 12.8 mL of isopropanol was added dropwise and the resulting mixture was stirred for a minimum of 30 minutes at this temperature. The resulting suspension was cooled down and stirred for 1 hour at 20-25° C. followed by 1 hour at 10-15° C. The precipitated solid was filtered and washed with xylene to obtain a wet solid. Yield: 65.2%. Purity (HPLC): 99.76%.

Example 7: Purification of Lofexidine Hydrochloride Compound 1·HCl 15.3 g of wet Lofexidine hydrochloride obtained in Example 5 were suspended in 120 mL of isopropanol at 20-25° C. The resulting mixture was heated up to reflux temperature and stirred at this temperature until complete dissolution. The resulting solution was cooled down to 20-25° C. and stirred for 1 hour at this temperature. After distillation of about 60 mL of isopropanol under reduced pressure, the resulting suspension was cooled down to 5-10° C. and stirred for 1 hour at this temperature. The resulting suspension was filtered, washed with isopropanol and dried under vacuum until constant weight to obtain Lofexidine hydrochloride. Yield: 50%. Purity: 99.89%.

Example 8: Purification of Lofexidine Hydrochloride Compound 1 HCl

The wet Lofexidine hydrochloride obtained in Example 6 was suspended in 30 mL of isobutanol at 20-25° C. The resulting mixture was heated up to reflux temperature and stirred at this temperature until complete dissolution. The resulting solution was cooled down to 5-10° C., and stirred for 1 hour at this temperature. The resulting suspension was filtered, washed with isobutanol and dried under vacuum until constant weight to obtain Lofexidine hydrochloride. Yield: 50%. Purity: 99.87%.

Example 9: Preparation of Ethyl 2-(2,6-Dichlorophenoxy)Propanoate Compound 2'

1.03 kg of 2,6-dichlorophenol were dissolved in 15.54 kg of dimethyl sulfoxide at 20-25° C., under nitrogen atmosphere. 0.44 kg of potassium carbonate were added at 20-25° C. while stirring. 0.87 kg of ethyl 2-chloropropionate and 1.50 kg of dimethyl sulfoxide were then added to the resulting suspension and the resulting mixture was stirred for 4 hours at 60-65° C. After cooling it down to 20-25° C., 13.43 kg of toluene followed by 15.49 kg of deionised water were added. The resulting mixture was allowed to settle and a biphasic solution was obtained. The aqueous layer was removed, and after two consecutive washes using an aqueous solution of potassium carbonate 10% (w/w) and a final wash with deionised water, the resulting organic layer was collected and concentrated to dryness under reduced pressure to obtain Ethyl 2-(2,6-dichlorophenoxy)propanoate as a liquid. Yield: 84.2%. Purity (HPLC): 99.68%.

Example 10: Preparation of 2-(1-(2,6-Dichlorophenoxy)Ethyl)-4,5-Dihydro-1H-Imidazole Monohydrochloride (Lofexidine Hydrochloride) Compound 1·HCl A solution of 0.89 kg of ethyl 2-(2,6-dichlorophenoxy) propanoate in 3.10 kg of toluene was added to a solution of 1.39 kg of aluminium isopropoxide and 0.41 kg of ethylenediamine in 8.53 kg of toluene at 20-25° C. while stirring under nitrogen atmosphere. The resulting mixture was heated up to 105° C. and stirred at this temperature until the reaction was completed. The mixture was cooled down to 10-15° C. Then, 0.45 kg of celite and 1.13 kg of isopropanol were added, followed by the dropwise addition of 4.47 kg of deionised water at 10-15° C. The resulting mixture was stirred for 1 hour at 20-25° C. and the resulting solid was filtered. The filtered solution was allowed to settle and a biphasic mixture was obtained. Then, the aqueous layer was removed and the resulting organic layer was washed with 2.68 kg of deionised water. After heating the resulting organic solution up to 45-50° C., a solution of 0.13 kg of hydrogen chloride gas in 0.7 Kg of isopropanol was added dropwise. The resulting suspension was stirred for 30 minutes at this temperature, cooled down and stirred for 30 minutes at 20-25° C. followed by 1 hour at 10-15° C. The precipitated solid was filtered and washed with toluene to obtain a wet solid. The resulting wet Lofexidine hydrochloride was suspended in 4.24 kg of isopropanol at 20-25° C. The resulting mixture was heated up to reflux temperature and stirred at this temperature until complete dissolution. The resulting solution was cooled down to 20-25° C. in 1 hour while stirring. After distillation of 2.12 kg of isopropanol under reduced pressure, the resulting suspension was cooled down to 5-10° C. and stirred for 1 hour at this temperature. The resulting suspension was filtered, washed with isopropanol and dried under vacuum until constant weight to obtain Lofexidine hydrochloride. Yield: 57.8%. Purity: 99.88%.

What is claimed is:

1. A process for preparing lofexidine, the compound of formula (1), or a pharmaceutically acceptable acid addition salt thereof, which comprises the step of:
   a) converting a compound of formula (3) into lofexidine in a solvent in the presence of an aluminium alkoxide of formula Al(OR$^2$)$_3$,

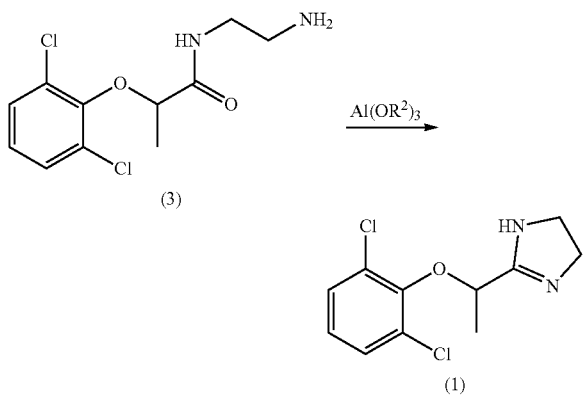

wherein R$^2$ is an alkyl having 1 to 11 carbon atoms, and
   b) optionally converting the lofexidine into a pharmaceutically acceptable salt thereof.

2. The process according to claim 1, wherein the lofexidine obtained in step (a) is converted into a pharmaceutically acceptable salt thereof.

3. The process according to claim 2, wherein the lofexidine obtained in step (a) is not isolated and is converted in situ into a pharmaceutically acceptable salt thereof.

4. The process according to claim 3, wherein the pharmaceutically acceptable salt of lofexidine is the hydrochloride salt.

5. The process according to claim 1, wherein the aluminium alkoxide of formula Al(OR$^2$)$_3$ is selected from the group comprising aluminium tributoxide, aluminium tri-sec-butoxide, aluminium tri-tert-butoxide and aluminium triisopropoxide.

6. The process according to claim 5, wherein the aluminium alkoxide of formula Al(OR$^2$)$_3$ is aluminium triisopropoxide.

7. The process according to claim 1, which further comprises a previous step of reacting a compound of formula (2) with ethylenediamine to provide a compound of formula (3),

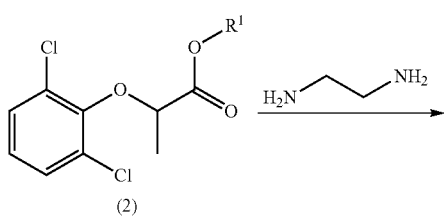

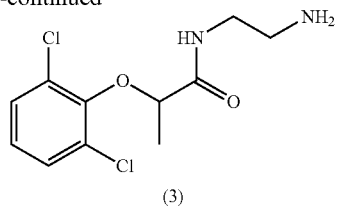

wherein R$^1$ is an alkyl having 1 to 11 carbon atoms.

8. The process according to claim 7, wherein the compound of formula (3) is isolated prior to the conversion step to lofexidine.

9. The process according to claim 7, wherein the compound of formula (3) is converted in situ to lofexidine without isolation.

10. The process according to claim 7, wherein the alkyl in R$^1$ is selected from the group consisting of methyl, ethyl, and linear or branched propyl, butyl, pentyl, hexyl, heptyl, octyl, nonyl, decyl and undecyl.

11. The process according to claim 10, wherein R$^1$ is ethyl.

12. The process according to claim 7, which further comprises a previous step of reacting 2,6-dichlorophenol, the compound of formula (4), or a salt thereof, in particular an alkaline salt thereof, with a compound of formula (5) in the presence of a solvent to prepare the compound of formula (2)

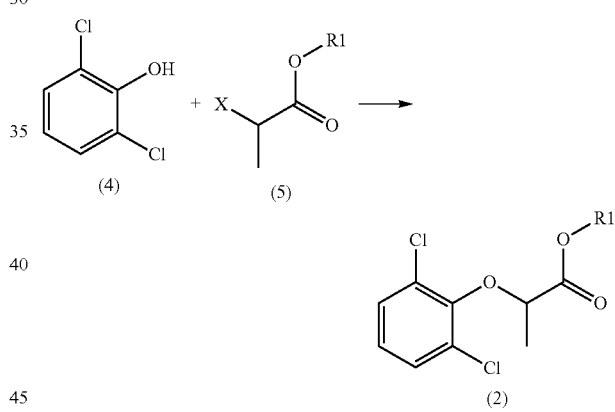

wherein R$_1$ is an alkyl having 1 to 11 carbon atoms and X is a leaving group.

13. The process according to claim 12, wherein the compound of formula (4) is used in the form of a salt which is the potassium salt.

14. The process according to claim 12, wherein the leaving group is selected from the group consisting of Cl, Br, I, methanesulfonate, trifluoromethanesulfonate, p-toluenesulfonate and benzenesulfonate.

15. The process according to claim 14, wherein the leaving group is Cl.

* * * * *